(12) United States Patent
James (10) Patent No.: US 11,515,042 B1
(45) Date of Patent: Nov. 29, 2022

(54) METHOD FOR GENERATING A DIAGNOSIS MODEL CAPABLE OF DIAGNOSING MULTI-CANCER ACCORDING TO STRATIFICATION INFORMATION BY USING BIOMARKER GROUP-RELATED VALUE INFORMATION, METHOD FOR DIAGNOSING MULTI-CANCER BY USING THE DIAGNOSIS MODEL, AND DEVICE USING THE SAME

(71) Applicant: KKL CONSORTIUM LIMITED, Tortola (VG)

(72) Inventor: Lancelot Fitzgerald James, Hong Kong (HK)

(73) Assignee: KKL Consortium Limited, Tortola (VG)

( * ) Notice: Subject to any disclaimer, the term of this patent is extended or adjusted under 35 U.S.C. 154(b) by 0 days.

(21) Appl. No.: 17/511,775

(22) Filed: Oct. 27, 2021

(51) Int. Cl.
*G16H 50/20* (2018.01)
*A61B 5/00* (2006.01)

(52) U.S. Cl.
CPC .......... *G16H 50/20* (2018.01); *A61B 5/7267* (2013.01); *A61B 5/7275* (2013.01)

(58) Field of Classification Search
CPC ...... G16H 50/20; A61B 5/7267; A61B 5/7275

USPC ............................................................ 705/2
See application file for complete search history.

(56) References Cited

U.S. PATENT DOCUMENTS

| | | | |
|---|---|---|---|
| 2021/0065011 A1* | 3/2021 | Liu | G06N 3/084 |
| 2021/0192225 A1* | 6/2021 | Kim | G06K 9/6256 |
| 2021/0233611 A1* | 7/2021 | Brewer | G16B 25/10 |
| 2022/0108459 A1* | 4/2022 | Lyu | A61B 6/037 |

* cited by examiner

*Primary Examiner* — Michael Tomaszewski
*Assistant Examiner* — Rachael Sojin Stone
(74) *Attorney, Agent, or Firm* — Taft Stettinius & Hollister LLP (57) ABSTRACT

A method for generating a diagnosis model capable of diagnosing multi-cancer is provided. The method includes steps of: (a) in response to acquiring training data including (i) stratification-related values, (ii) biomarker group-related value information and (iii) its corresponding Ground Truth cancer information, setting initial prediction values of a base classification model capable of classifying cancers for each of the stratification-related values; and (b) generating a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model.

20 Claims, 4 Drawing Sheets

METHOD FOR GENERATING A DIAGNOSIS MODEL CAPABLE OF DIAGNOSING MULTI-CANCER ACCORDING TO STRATIFICATION INFORMATION BY USING BIOMARKER GROUP-RELATED VALUE INFORMATION, METHOD FOR DIAGNOSING MULTI-CANCER BY USING THE DIAGNOSIS MODEL, AND DEVICE USING THE SAME

FIELD OF THE DISCLOSURE

The present disclosure relates to a method for generating a diagnosis model capable of diagnosing multi-cancer according to stratification-related values of patients by using biomarker group-related value information, a method for diagnosing multi-cancer by using the diagnosis model and a device using the same; and more particularly, to the method for (i) stratifying the information on the patients that affects diagnosis of cancer and (ii) generating the diagnosis model capable of diagnosing cancer of the patients for each of strata, the method for diagnosing multi-cancer by using the diagnosis model and the device using the same.

BACKGROUND OF THE DISCLOSURE

Tumor metastasis represents that some portion of a tumor is detached from a part of a body of patient and moves to other parts of the body via blood, which is an important cause of cancer-related death. A general way of determining tumor status is a biopsy which detaches and examines a part of a tissue in an early stage of metastasis. It is, however, not easy to determine a part of the body from which the tissue is removed. As an alternative way, a liquid biopsy attracting attention in recent years can detect tumor cells in a biological sample such as blood, urine, etc. derived from the body of patient. According to the liquid biopsy, a cancer in the early stage can be detected and diagnosed and additionally the progression of cancer and its corresponding cure can be monitored.

A biomarker is a measurable indicator of some biological state or condition. Biomarkers are often measured and evaluated using blood, urine, or soft tissues to examine normal biological processes, pathogenic processes, or pharmacologic responses to a therapeutic intervention. The biomarkers can detect changes in the body by using proteins, nucleic acids, and metabolites contained in biological samples.

However, since there is a limit in diagnosing cancers with a biomarker, a cancer diagnosing method using complex biomarkers with an improvement in diagnostic sensitivity and specificity is currently used in this field.

However, in case of predicting a certain cancer by using such complex biomarkers, a specific biomarker included in the complex biomarkers may not only represent an indicator for the certain cancer but also represent another indicator for another cancer. Thus, the certain cancer may be wrongly predicted by using the complex biomarkers.

As an example, it may indicate the adenocarcinoma as a result of prediction by using biomarker group-related value information derived from the complex biomarkers, although a patient's cancer is actually squamous cell carcinoma.

Also, in predicting cancers by using the biomarker group-related value information of the complex biomarkers, there is a possibility of acquiring a different result according to two or more judge.

Thus, various methodologies have been suggested to classify cancers by using the biomarker group-related value information of the complex biomarkers.

Particularly, variables, such as gender, age, etc., which have large influence on physiological features of patients have to be considered in training of a diagnosis model using the biomarker group-related value information.

For this, recently, a method of (i) stratifying data of the patients by using information of the patients and (ii) training different classifying model for each of strata by using the information of the patient for each of the strata.

However, in a stage of training classification model for each of the strata, the method is intuitive in that the method use only stratified data, there is a problem in that reliability is not secured due to large variance of estimated model because the number of pieces of the stratified data is small in case the number of the strata is large.

Accordingly, an applicant of the present disclosure provides a diagnosis model capable of diagnosing cancers of patients, by using the biomarker group-related value information, for each of the strata without a degradation of the reliability caused by increasing of the variance.

SUMMARY OF THE DISCLOSURE

It is an object of the present disclosure to solve all the aforementioned problems.

It is still another object of the present disclosure to provide a diagnosis model capable of diagnosing cancers of patients for each of strata in which each corresponding variance is minimized by using biomarker group-related value information.

It is still yet another object of the present disclosure to recognize types of cancers for each of strata of patients accurately by using the biomarker group-related value information for diagnosing multi-cancer.

It is still yet another object of the present disclosure to recognize types of cancers according to the strata of patients accurately by statistical determination method using the biomarker group-related value information for diagnosing multi-cancer.

It is still yet another object of present the disclosure to improve a reliability of determination of cancer according to the strata of patients by the statistical determination method using the biomarker group-related value information for diagnosing multi-cancer.

In order to accomplish objects above and characteristic effects to be described later of the present disclosure, distinctive configurations of the present disclosure are described as follows.

In accordance with one aspect of the present disclosure, there is provided a method for generating a diagnosis model capable of diagnosing multi-cancer according to stratification-related values of patients by using biomarker group-related value information including steps of: (a) a diagnosis model generating device, in response to acquiring n pieces of training data including (i) the stratification-related values corresponding to K stratification-related variables, (ii) the biomarker group-related value information and (iii) its corresponding Ground Truth cancer information for each of the patients, setting initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (b) the diagnosis model generating device generating a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model, wherein, during a t-th iteration at the step of (b) wherein t is an integer of 1 or more and T or less, the diagnosis model generating device performs processes of: (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree, to thereby generate a t-th classification model.

As one example, wherein the base classification model includes (i) a first classification model, which is a total classification model, capable of classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

As one example, wherein, at the step of (b), the diagnosis model generating device (i) makes a (t-1)-th total decision tree branch off from a (t-1)-th total classification model by using the total residuals corresponding to the n pieces of training data and a preset first normalization parameter such that a total correlation generated by referring to the total residuals and the first normalization parameter is maximized, (ii) makes (t-1)-th stratification-related variable decision trees branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) makes (t-1)-th stratification-related value decision trees branch off from a (t-1)-th stratification-related value classification model by using each of the total residuals corresponding to the n pieces of training data and a preset third normalization parameter such that each of stratification-related value correlations generated by referring to stratification-related value residuals corresponding to each of the stratification-related values and the third normalization parameter is maximized and (iv) generate a certain decision tree, that has the largest correlation among the (t-1)-th total decision tree, the (t-1)-th stratification-related variable decision trees and the (t-1)-th stratification-related value decision trees, as the t-th decision tree.

As one example, wherein, at the step of (b), the diagnosis model generating device updates the (t-1)-th classification model by applying at least one preset weight whose range is greater than zero and less than one to the t-th decision tree.

As one example, wherein the diagnosis model generating device applies the weight to a t-th decision tree classification model corresponding to the t-th decision tree and generates the t-th classification model by taking a sum of (i) the t-th decision tree classification model to which the weight has been applied and (ii) the (t-1)-th classification model.

As one example, wherein, at the step of (b), the diagnosis model generating device (i) generates losses by using the Ground Truth cancer information and the (t-1)-th cancer-predicting values and (ii) generates the total residuals by differentiating the losses.

In accordance with another aspect of the present invention, there is provided a method for generating a diagnosis model capable of diagnosing multi-cancer according to stratification-related values of patients by using biomarker group-related value information including steps of: (a) on the condition that (1) a diagnosis model generating device, in response to acquiring n pieces of training data including (i) the stratification-related values corresponding to K stratification-related variables, (ii) the biomarker group-related value information and (iii) its corresponding Ground Truth cancer information for each of the patients, has set initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (2) the diagnosis model generating device has generated a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model, wherein, during a t-th iteration at the (2) wherein t is an integer of 1 or more and T or less, the diagnosis model generating device has performed processes of: (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree, to thereby generate a t-th classification model, a multi-cancer diagnosis device acquiring certain stratification-related values and certain biomarker group-related value information of a certain patient; and (b) the multi-cancer diagnosis device (i) inputting the certain stratification-related values and the certain biomarker group-related value information into the diagnosis model and (ii) instructing the diagnosis model to output certain cancer information which is a result of classifying cancers based on the certain biomarker group-related value information via a certain classification model corresponding to the certain stratification-related values of the certain patient.

As one example, wherein the base classification model includes (i) a first classification model, which is a total classification model, classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

As one example, wherein, at the step of (a), by the diagnosis model generating device, (i) a (t-1)-th total decision tree has been made to branch off from a (t-1)-th total classification model by using the total residuals corresponding to the n pieces of training data and a preset first normalization parameter such that a total correlation generated by referring to the total residuals and the first normalization parameter is maximized, (ii) (t-1)-th stratification-related variable decision trees have been made to branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) (t-1)-th stratification-related value decision trees have been made to branch off from a (t-1)-th stratification-related value classification model by using each of the total residuals corresponding to the n pieces of training data and a preset third normalization parameter such that each of stratification-related value correlations generated by referring to stratification-related value residuals and the third normalization parameter is maximized and (iv) a certain decision tree has been generated such that the certain decision tree has the largest correlation among the (t-1)-th total decision tree, the (t-1)-th stratification-related variable decision trees and the (t-1)-th stratification-related value decision trees, as the t-th decision tree.

As one example, wherein, at the step of (a), by the diagnosis model generating device, the (t-1)-th classification model has been updated by applying at least one preset weight whose range is greater than zero and less than one to the t-th decision tree.

In accordance with still another aspect of the present invention, there is provided a diagnosis model generating device capable of diagnosing multi-cancer according to stratification-related values of patients by using biomarker group-related value information including: one or more memories that stores instructions; and at least one processor configured to execute the instructions to perform processes of (I) in response to acquiring n pieces of training data including (i) the stratification-related values corresponding to K stratification-related variables, (ii) the biomarker group-related value information and (iii) its corresponding Ground Truth cancer information for each of the patients, setting initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (II) generating a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model, wherein, during a t-th iteration at the process of (II) wherein t is an integer of 1 or more and T or less, the processor performs processes of: (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree, to thereby generate a t-th classification model.

As one example, the base classification model includes (i) a first classification model, which is a total classification model, capable of classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

As one example, at the process of (II), the processor (i) makes a (t-1)-th total decision tree branch off from a (t-1)-th total classification model by using the total residuals corresponding to the n pieces of training data and a preset first normalization parameter such that a total correlation generated by referring to the total residuals and the first normalization parameter is maximized, (ii) makes (t-1)-th stratification-related variable decision trees branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) makes (t-1)-th stratification-related value decision trees branch off from a (t-1)-th stratification-related value classification model by using each of the total residuals corresponding to the n pieces of training data and a preset third normalization parameter such that each of stratification-related value correlations generated by referring to stratification-related value residuals corresponding to each of the stratification-related values and the third normalization parameter is maximized and (iv) generate a certain decision tree, that has the largest correlation among the (t-1)-th total decision tree, the (t-1)-th stratification-related variable decision trees and the (t-1)-th stratification-related value decision trees, as the t-th decision tree.

As one example, at the process of (II), the processor updates the (t-1)-th classification model by applying at least one preset weight whose range is greater than zero and less than one to the t-th decision tree.

As one example, the processor applies the weight to a t-th decision tree classification model corresponding to the t-th decision tree and generates the t-th classification model by taking a sum of (i) the t-th decision tree classification model to which the weight has been applied and (ii) the (t-1)-th classification model.

As one example, at the process of (II), the processor (i) generates losses by using the Ground Truth cancer information and the (t-1)-th cancer-predicting values and (ii) generates the total residuals by differentiating the losses.

In accordance with still another aspect of the present invention, there is provided a multi-cancer diagnosis device capable of diagnosing multi-cancer according to stratification-related values of patients by using biomarker group-related value information including: one or more memories that stores instructions; and at least one processor configured to execute the instructions to perform processes of (I) on the condition that (1) a diagnosis model generating device, in response to acquiring n pieces of training data including (i) the stratification-related values corresponding to K stratification-related variables, (ii) the biomarker group-related value information and (iii) its corresponding Ground Truth cancer information for each of the patients, has set initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (2) the diagnosis model generating device has generated a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model, wherein, during a t-th iteration at the (2) wherein t is an integer of 1 or more and T or less, the diagnosis model generating device has performed processes of: (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree, to thereby generate a t-th classification model, acquiring certain stratification-related values and certain biomarker group-related value information of a certain patient; and (II) (i) inputting the certain stratification-related values and the certain biomarker group-related value information into the diagnosis model and (ii) instructing the diagnosis model to output certain cancer information which is a result of classifying cancers based on the certain biomarker group-related value information via a certain classification model corresponding to the certain stratification-related values of the certain patient.

As one example, the base classification model includes (i) a first classification model, which is a total classification model, classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

As one example, at the process of (I), by the diagnosis model generating device, (i) a (t-1)-th total decision tree has been made to branch off from a (t-1)-th total classification model by using the total residuals corresponding to the n pieces of training data and a preset first normalization parameter such that a total correlation generated by referring to the total residuals and the first normalization parameter is maximized, (ii) (t-1)-th stratification-related variable decision trees have been made to branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) (t-1)-th stratification-related value decision trees have been made to branch off from a (t-1)-th stratification-related value classification model by using each of the total residuals corresponding to the n pieces of training data and a preset third normalization parameter such that each of stratification-related value correlations generated by referring to stratification-related value residuals and the third normalization parameter is maximized and (iv) a certain decision tree has been generated such that the certain decision tree has the largest correlation among the (t-1)-th total decision tree, the (t-1)-th stratification-related variable decision trees and the (t-1)-th stratification-related value decision trees, as the t-th decision tree.

As one example, at the process of (I), by the diagnosis model generating device, the (t-1)-th classification model has been updated by applying at least one preset weight whose range is greater than zero and less than one to the t-th decision tree.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

In the following detailed description, reference is made to the accompanying drawings that show, by way of illustration, specific embodiments in which the disclosure may be practiced. These embodiments are described in sufficient detail to enable those skilled in the art to practice the disclosure. It is to be understood that the various embodiments of the present disclosure, although different, are not necessarily mutually exclusive. For example, a particular feature, structure, or characteristic described herein in connection with one embodiment may be implemented within other embodiments without departing from the spirit and scope of the present disclosure. In addition, it is to be understood that the position or arrangement of individual elements within each disclosed embodiment may be modified without departing from the spirit and scope of the present disclosure. The following detailed description is, therefore, not to be taken in a limiting sense, and the scope of the present disclosure is defined only by the appended claims, appropriately interpreted, along with the full range of equivalents to which the claims are entitled. In the drawings, like numerals refer to the same or similar components throughout the several aspects.

To allow those skilled in the art to the present disclosure to be carried out easily, the example embodiments of the present disclosure by referring to attached diagrams will be explained in detail as shown below.

Figure 1:
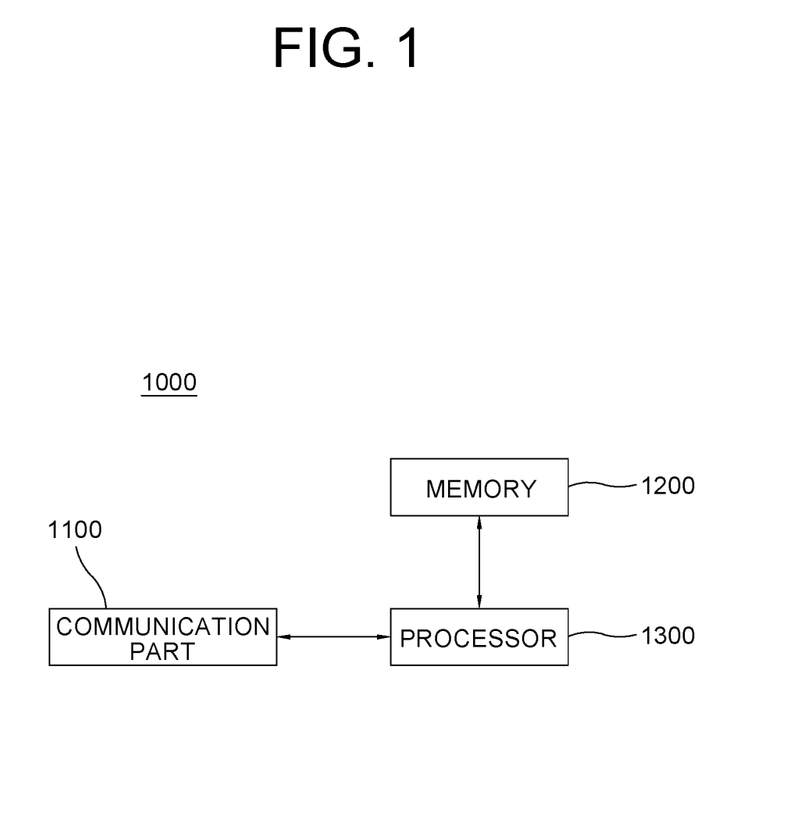
FIG. 1 is a drawing schematically illustrating a diagnosis model generating device for generating diagnosis model capable of diagnosing multi-cancer according to stratification-related values of patients by using biomarker group-related value information in accordance with one example embodiment of the present disclosure.

FIG. 1 is a drawing schematically illustrating a diagnosis model generating device for generating diagnosis model capable of diagnosing multi-cancer according to stratification-related values of patients by using biomarker group-related value information in accordance with one example embodiment of the present disclosure.

Referring to FIG. 1, the diagnosis model generating device 1000 in accordance with one example embodiment of the present disclosure may include (i) a communication part 1100 for acquiring n pieces of training data including stratification-related values corresponding to K stratification-related variables for each of patients, the biomarker group-related value information for each of patients and its corresponding Ground Truth cancer information for each of patients, (ii) a memory 1200 that stores instructions for generating the diagnosis model capable of diagnosing multi-cancer according to the stratification-related values of patients by using the n pieces of training data acquired from the communication part 1100 and (iii) a processor 1300 that performs, according to the instructions stored in the memory 1200, a process of generating the diagnosis model capable of diagnosing multi-cancer according to the stratification-related values of patients by using the n pieces of training data acquired from the communication part 1100. The n and K may be an integer of 1 or more.

Herein, the communication part 1100 may acquire the n pieces of training data (i) from other devices in which the n pieces of training data are stored or (ii) through a user input.

Specifically, the diagnosis model generating device 1000 may achieve desired system performance by using typically combinations of a computing device, e.g., a computer processor, a memory, a storage, an input device, an output device, and other devices that may include components of conventional computing devices; an electronic communication device such as a router or a switch; an electronic information storage system such as a network-attached storage (NAS) device and a storage area network (SAN), and computer software, i.e., instructions that allow the computing device to function in a specific way.

Also, the processor of such devices may include hardware configuration of MPU (Micro Processing Unit) or CPU (Central Processing Unit), cache memory, data bus, etc. Additionally, OS and software configuration of applications that achieve specific purposes may be further included.

However, computing device does not exclude an integrated device including any combination of a processor, a memory, a medium, or any other computing components for implementing the present disclosure.

A method for generating the diagnosis model by using the diagnosis model generating device configured as such in accordance with one example of the present disclosure is described by referring to FIG. 2 as follows.

First, at a step of S1100, the diagnosis model generating device 1000 may acquire the n pieces of training data.

As an example, the diagnosis model generating device 1000, via the communication part, may acquire the n pieces of training data from other devices in which the n pieces of training data are stored or from the user input. The n may be an integer of 1 or more.

Herein, the n pieces of training data may include information on each of the patients, the biomarker group-related value information for each of patients and its corresponding Ground Truth cancer information for each of patients. Herein, the Ground Truth cancer information for each of patients may be cancer information that each of the patients actually has. Further, the number of cancer information is one or more. Also, the information on each of the patients may be the stratification-related values corresponding to the K stratification-related variables. The K may be an integer of 1 or more. As an example, in case genders, age groups, etc. of the patients are taken as the stratification-related variables, the stratification-related values may be male 10s, female 10s, male 20s, female 30s, etc. However, the scope of the present disclosure is not limited thereto and the K stratification-related variables may include various information in various categories related to the patients such as weight, height, etc.

Meanwhile, the biomarker group-related value information may be value information, for diagnosing multi-cancer, related to each of biomarkers. Herein, a biomarker may be an indicator value for diagnosing cancer using proteins, nucleic acids, and metabolites contained in a biological sample such as blood, urine, etc. derived from a patients' body.

Next, at a step of S1200, the diagnosis model generating device 1000 may initialize a base classification model capable of classifying multi-cancer according to the stratification-related values of patients by using the biomarker group-related value information from the n pieces of training data. That is, the diagnosis model generating device 1000 may set initial prediction values of the base classification model. As an example, the diagnosis model generating device 1000 may generate a weak learner by setting the initial prediction value as zero.

Meanwhile, the base classification model can be configured as follows.

An input variable x of the classification model may be covariate. For example, the input variable x may be a vector of p-dimension including patients' information, the biomarker group-related value information, etc. An output variable y, that is, a response variable, may include L classes for classifying multi-cancer and may be depicted as y ∈ {1, . . . , L}.

Therefore, a logistic classification model which predicts a class of the output variable y by using the input variable x can be defined as follows.

$$F(x) = \begin{pmatrix} F_{(1)}(x) \\ \cdots \\ F_{(L)}(x) \end{pmatrix} = \beta_1 x + \beta_0$$

Also, a probability corresponding to the output variable can be depicted as follows.

$$P_r(y = l) = \frac{e^{F_{(l)}(x)}}{e^{F_{(1)}(x)} + \ldots + e^{F_{(L)}(x)}} \quad l \in \{1, \ldots, L\}$$

The logistic classification model F can be depicted as linear combination of the input variable x. That is, a function space of the logistic classification model can be depicted as follows.

$$F=\{F(x):F(x)=\beta_1 x_1+\cdots+\beta_p x_p, \beta_i \in \mathbb{R}, i=1, \ldots, p\}$$

Similar to above, a boosting classification model using decision trees can be depicted as follows. The boosting classification model using the decision trees can be represented as linear combination of the decision trees whose depths are two or three and its function space can be depicted as below.

$$\overline{F}_0 = \{F(x):F(x) = \gamma_1 f_1(x) + \ldots + \gamma_M f_M,$$
$$f_i(x) \in \overline{F}_B, \gamma_i \in R, i=1, \ldots, M\}$$
$$\overline{F}_B = \{f:f \text{ is a decision tree whose depth is two or three}, |f|_\infty \leq 1\}$$

Therefore, the base classification model capable of classifying L cancer classes according to the stratification-related values of patients by using the biomarker group-related value information can be depicted as follows. That is, the base classification model under certain function spaces of $\overline{F}_0$, $\overline{F}_{z_k^j}$, $\overline{F}_{z_{k1}^{j1} z_{k2}^{j2}}$ and functions of $F_0$, $F_{z_k^j}$, $F_{z_{k1}^{j1} z_{k2}^{j2}}$ can be depicted as follows.

$$F(x, z_1, \ldots, z_k) =$$
$$F_0(x) + \sum_{k=1}^{K} \sum_{j=1}^{c_k} F_{z_k^j}(x; z_k^j) + \sum_{k_1=1}^{K-1} \sum_{k_2:k_2>k_1} \sum_{j_1=1}^{c_{k_1}} \sum_{j_2=1}^{c_{k_2}} F_{z_{k1}^{j1} z_{k2}^{j2}}(x; z_{k1}^{j1}, z_{k2}^{j2})$$

Under the base classification model, $z_k$, k=1,2, ···, K are variables for representing each of strata and each of the variables can take $c_k$ values. That is, $z_k \in \{z_k^1, \ldots, z_k^{c_k}\}$ As an example, in case (i) a male and a female are taken as a variable of gender and (ii) teens, twenties, thirties are taken as a variable of age, $z_k$ can be the variable of the gender or the variable of the age. The variable of the gender can take two values, i.e., male or female, and the variable of the age can take three values, i.e., teens, twenties, thirties.

Also, each of functions in the base classification model can be depicted as follows.

$$F_0(x) \in \overline{F}_0$$

$$F_{z_k^j}(x; z_k^j) = F_{z_k^j}(x) I(z_k = z_k^j)$$
$$F_{z_{k1}^{j1} z_{k2}^{j2}}(x; z_{k1}^{j1}, z_{k2}^{j2}) = F_{z_{k1}^{j1} z_{k2}^{j2}}(x) I(z_{k1} = z_{k1}^{j1}) I(z_{k2} = z_{k2}^{j2})$$

Herein, I may be an indicator function.

That is, a function $F_0(x)$ may be a first classification model, which is a total classification model, capable of classifying cancers by using all pieces of the biomarker group-related value information regardless of the stratification-related values of patients, a function $F_{z_k^j}$ may be a second classification model, which is a stratification-related variable classification model, capable of classifying cancers by using the biomarker group-related value information for each of the K stratification-related variables and a function $F_{z_{k1}^{j1} z_{k2}^{j2}}$ may be a third classification model, which is a stratification-related value classification model, capable of classifying cancers by using the biomarker group-related value information for each of the stratification-related values.

Therefore, the classification model in accordance with the present disclosure, via the indicator function, only has an effect on a specific variable among the stratification-related variables according to a specific stratification-related values belonging to the specific variable, thereby training different classification models for each of the stratification-related values of patients. Accordingly, the classification model capable of classifying cancers according to the stratification-related values of patients may be generated.

Next, the diagnosis model generating device 1000 generates a decision tree for each of learning iterations at a step of S1300, updates the classification model by using the decision tree at a step of S1400, and generates the classification model according to each of pieces of the stratification-related values of patients at a step of S1500.

That is, a first decision tree to a T-th decision tree may be generated by using a previous classification model, to thereby generate the diagnosis model. Herein the previous classification model has been updated by its corresponding previous iteration via a first iteration to a T-th iteration. The T may be an integer of 1 or more. Herein, the previous classification model may represent the base classification model at the first iteration.

As an example, during a t-th iteration which is an iteration among the first iteration to the t-th iteration, the diagnosis model generating device 1000 inputs the n pieces of training data into a (t-1)-th classification model which is the previous classification model at the t-th iteration and instructs the (t-1)-th classification model to output (t-1)-th cancer-predicting values which are results of classifying cancers for each of the n pieces of training data.

And, the diagnosis model generating device 1000 may generate each of total residuals for each of the n training data by referring to the (t-1)-th cancer-predicting values and the Ground Truth cancer information for each of the patients.

That is, the diagnosis model generating device 1000 may generate losses L by using the Ground Truth cancer information for each of the n training data and the (t-1)-th cancer-predicting values and may generate the total residuals r by differentiating the losses. The L and the r may be depicted in mathematical form as follows.

$$L = \sum_{i=1}^{n} L_i = \sum_{i=1}^{n} \{\log(1 + \exp(-2y_i F_i^{t-1}))\}, \text{ where}$$

$$F_i^t := F^t(x_i, z_{i1}, z_{i2}, \ldots, z_{iK})$$

$$r^{t-1} := -\frac{\partial L}{\partial F}\bigg|_{F^{t-1}} = \left(\frac{2y_i \exp(-2y_i F_i^{t-1})}{1 + (-2y_i F_i^{t-1})}\right)_{i=1, \ldots, n}$$

Herein, $y_i$ may be the Ground Truth cancer information.

And, the diagnosis model generating device 1000 generates a t-th decision tree that maximizes a correlation with the total residuals and updates the (t-1)-th classification model by using the t-th decision tree, to thereby generate a t-th classification model.

Meanwhile, a process of generating the t-th decision tree by using residuals for each of the n pieces of training data may be explained more specifically as follows.

The diagnosis model generating device 1000 makes a (t-1)-th total decision tree branch off from a (t-1)-th total classification model by using the total residuals corresponding to the n pieces of training data and a preset first normalization parameter such that a total correlation generated by referring to the total residuals and the first normalization parameter is maximized.

That is, the diagnosis model generating device 1000 makes a decision tree, depicted as below, branch off by using data $(x_i, r_i^{t-1})$, $i=1, \ldots, n$ and a normalization parameter $\lambda_0$ such that a correlation $$\frac{1}{\lambda_0} \left| < r^{t-1}, f > \right|$$

is maximized.

$$\tilde{f}_0 := \operatorname{argmax} \left| < r^{t-1}, f > \right|, f \in \mathcal{F}_B$$

$$f_0 := \frac{\tilde{f}_0}{\lambda_0} C_0 := \frac{1}{\lambda_0} \left| < r^{t-1}, f_0 > \right|$$

Also, the diagnosis model generating device 1000 makes (t-1)-th stratification-related variable decision trees branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized.

That is, for each of the stratification-related variables $z_k^j$, $k=1,2,\ldots, K, j=1, \ldots, c_k$, the diagnosis model generating device 1000 makes a decision tree, depicted as below, branch off by using data $(x_i, r_i^{t-1})$, $i=1, \ldots, n$ and a normalization parameter $\lambda_1$ such that correlation $$\frac{1}{\lambda_1} \left| < r^{t-1}, f \cdot I(z_k = z_k^j) > \right|$$

is maximized.

$$\tilde{f}_{z_k^j} := \operatorname{argmax} \left| < r^{t-1}, f \cdot I(z_k = z_k^j) > \right|, f \in \mathcal{F}_B$$

$$f_{z_k^j} := \frac{\tilde{f}_{z_k^j} \cdot I(z_k = z_k^j)}{\lambda_1} \quad C_{z_k^j} := \frac{1}{\lambda_1} \left| < r^{t-1}, f_{z_k^j} > \right|$$

Also, the diagnosis model generating device 1000 makes (t-1)-th stratification-related value decision trees branch off from a (t-1)-th stratification-related value classification model by using each of the total residuals corresponding to the n pieces of training data and a preset third normalization parameter such that each of stratification-related value correlations generated by referring to stratification-related value residuals corresponding to each of the stratification-related values and the third normalization parameter is maximized.

That is, for each of the stratification-related values, $k_1 < k_2$, $k_1, k_2 \in \{1, \ldots, K\}$, $j_{k1}=1, \ldots, c_{k1}$, $j_{k2}=1, \ldots, c_{k2}$, the diagnosis model generating device 1000 makes a decision tree, depicted as below, branch off by using data $(x_i, r_i^{t-1})$, $i=1, \ldots, n$ and a normalization parameter $\lambda_2$ such that a correlation $$\frac{1}{\lambda_2} \left| < r^{t-1}, f \cdot I(z_{k1} = z_{k1}^{j_{k1}}) \cdot I(z_{k2} = z_{k2}^{j_{k2}}) > \right|$$

is maximized.

$$\tilde{f}_{z_{k1}^{j_{k1}} z_{k2}^{j_{k2}}} := \operatorname{argmax} \left| < r^{t-1}, f \cdot I(z_{k1} = z_{k1}^{j_{k1}}) \cdot I(z_{k2} = z_{k2}^{j_{k2}}) > \right|, f \in \mathcal{F}_B$$

$$f_{z_{k1}^{j_{k1}} z_{k2}^{j_{k2}}} := \frac{\tilde{f}_{z_{k1}^{j_{k1}} z_{k2}^{j_{k2}}} \cdot I(z_{k1} = z_{k1}^{j_{k1}}) \cdot I(z_{k2} = z_{k2}^{j_{k2}})}{\lambda_2}$$

$$C_{z_{k1}^{j_{k1}} z_{k2}^{j_{k2}}} := \frac{1}{\lambda_2} \left| < r^{t-1}, f_{z_{k1}^{j_{k1}} z_{k2}^{j_{k2}}} > \right|$$

After this, the diagnosis model generation device 1000 may generate a certain decision tree, that has the largest correlation among the (t-1)-th total decision tree, the (t-1)-th stratification-related variable decision trees and the (t-1)-th stratification-related value decision trees, as the t-th decision tree.

That is, an index set related to strata used in the learning process may be depicted as follows.

$$J := \{0\} \cup \{z_1^1, \ldots, z_1^{c1}, \ldots, z_K^1, \ldots, z_K^{cK}\} \cup \{z_1^1 z_2^1, \ldots, z_1^{c1} z_2^{c1}, \ldots, z_{K-1}^1 z_K^1, \ldots, z_{K-1}^{cK-1} z_K^K\}$$

Herein, let the largest index among the (t-1)-th total decision tree, (t-1)-th stratification-related variable decision trees and (t-1)-th stratification-related value decision trees be $z^*$ and let a decision tree added in the t-th iteration be $f_{z^*}$, then the t-th decision tree may be depicted as follows.

$$z^* = \operatorname{argmax}_{z \in J}\{C_z \mid z \in J\} f^t(x, z_1, z_2, \ldots, z_K) := f_{z^*}$$

And, the diagnosis model generating device 1000 may update the (t-1)-th classification model by applying at least one preset weight whose range is greater than zero and less than one to the t-th decision tree.

That is, the diagnosis model generating device 1000 may apply the weight to a t-th decision tree classification model corresponding to the t-th decision tree and may generate the t-th classification model by taking a sum of (i) the t-th decision tree classification model to which the weight has been applied and (ii) the (t-1)-th classification model as below.

$$F^t(x, z_1, z_2, \ldots, z_K) = F^{t-1}(x, z_1, z_2, \ldots, z_K) + \epsilon f^t(x, z_1, z_2, \ldots, z_K)$$

(predefined small $\epsilon > 0$)

Accordingly, the diagnosis model generating device 1000 may generate a classification model capable of classifying cancers for each of the stratification-related values by updating the classification model through T iterations.

On the condition that the diagnosis model has been generated as such, a method and a device for diagnosing multi-cancer by using the diagnosis model may be explained as follows.

Figure 3:
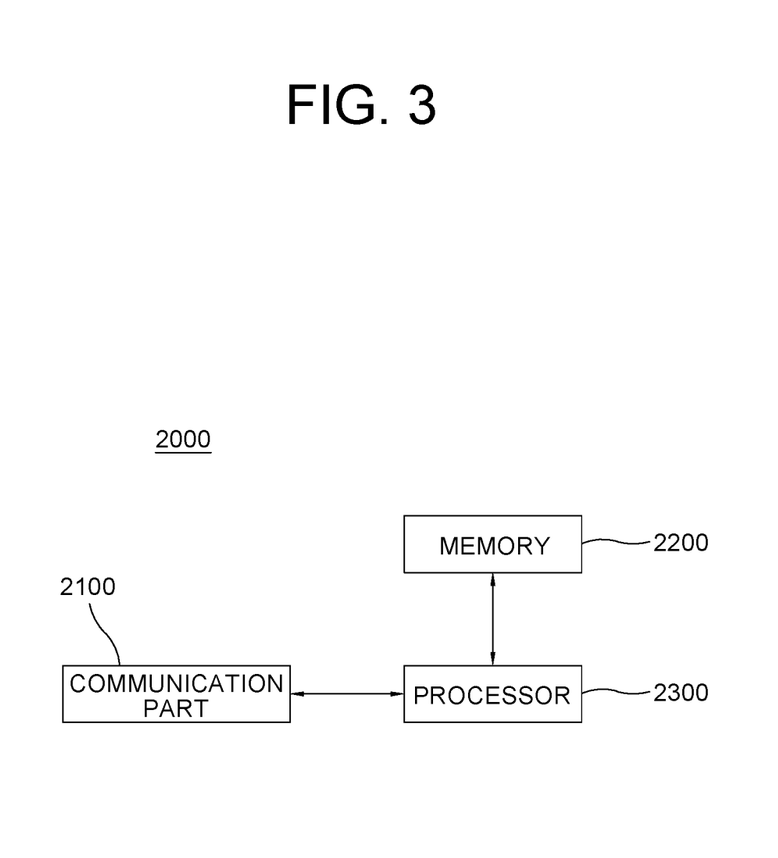
FIG. 3 is a drawing schematically illustrating a multi-cancer diagnosis device for diagnosing multi-cancer according to the stratification-related values of patients by using the biomarker group-related value information in accordance with one example embodiment of the present disclosure.

FIG. 3 is a drawing schematically illustrating a multi-cancer diagnosis device for diagnosing multi-cancer according to strata by using biomarker group-related value information for diagnosing multi-cancer.

Referring to FIG. 3, a multi-cancer diagnosis device 2000 in accordance with one example embodiment of the present disclosure may include (i) a communication part 2100 for performing a function of acquiring certain stratification-related values and certain biomarker group-related value information of a certain patient, (ii) a memory 2200 that stores instructions for diagnosing multi-cancer, by using the certain stratification-related values and the certain biomarker group-related value information of the certain patient acquired from the communication part 2100, according to the stratification-related values of patients and (iii) a processor 2300 for performing a operation of diagnosing multi-cancer, according to the instructions stored in the memory 2200, by using the certain stratification-related values and the certain biomarker group-related value information of the certain patient information acquired from the communication part 2100.

Herein, the communication part 2100 may acquire the certain stratification-related values and the certain biomarker group-related value information of the certain patient from other devices or from user input(s).

Specifically, the multi-cancer diagnosis device 2000 may achieve desired system performance by using combinations of a computing device, e.g., a computer processor, a memory, a storage, an input device, an output device, and other devices that may include components of conventional computing devices; an electronic communication device such as a router or a switch; an electronic information storage system such as a network-attached storage (NAS) device and a storage area network (SAN), and computer software, i.e., instructions that allow the computing device to function in a specific way.

Also, the processor of such devices may include hardware configuration of MPU (Micro Processing Unit) or CPU (Central Processing Unit), cache memory, data bus, etc. Additionally, OS and software configuration of applications that achieve specific purposes may be further included.

However, the computing device does not exclude an integrated device including any combination of a processor, a memory, a medium, or any other computing components for implementing the present disclosure.

Figure 4:
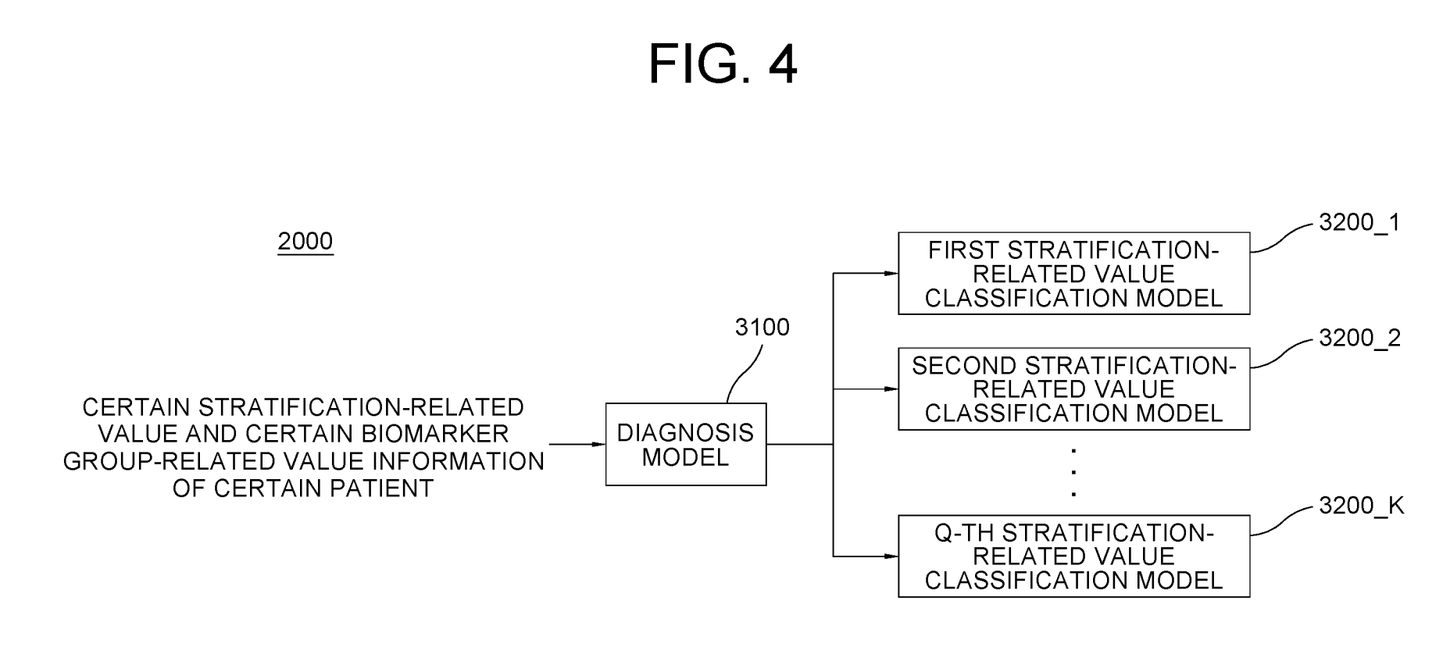
FIG. 4 is a drawing schematically illustrating a method of diagnosing multi-cancer according to the stratification-related values of patients by using the biomarker group-related value information in accordance with one example embodiment of the present disclosure.

Referring to FIG. 4, a method for diagnosing multi-cancer by using a multi-cancer diagnosis device capable of diagnosing multi-cancer according to the stratification-related values of patients by using biomarker group-related value information may be explained as follows.

Figure 2:
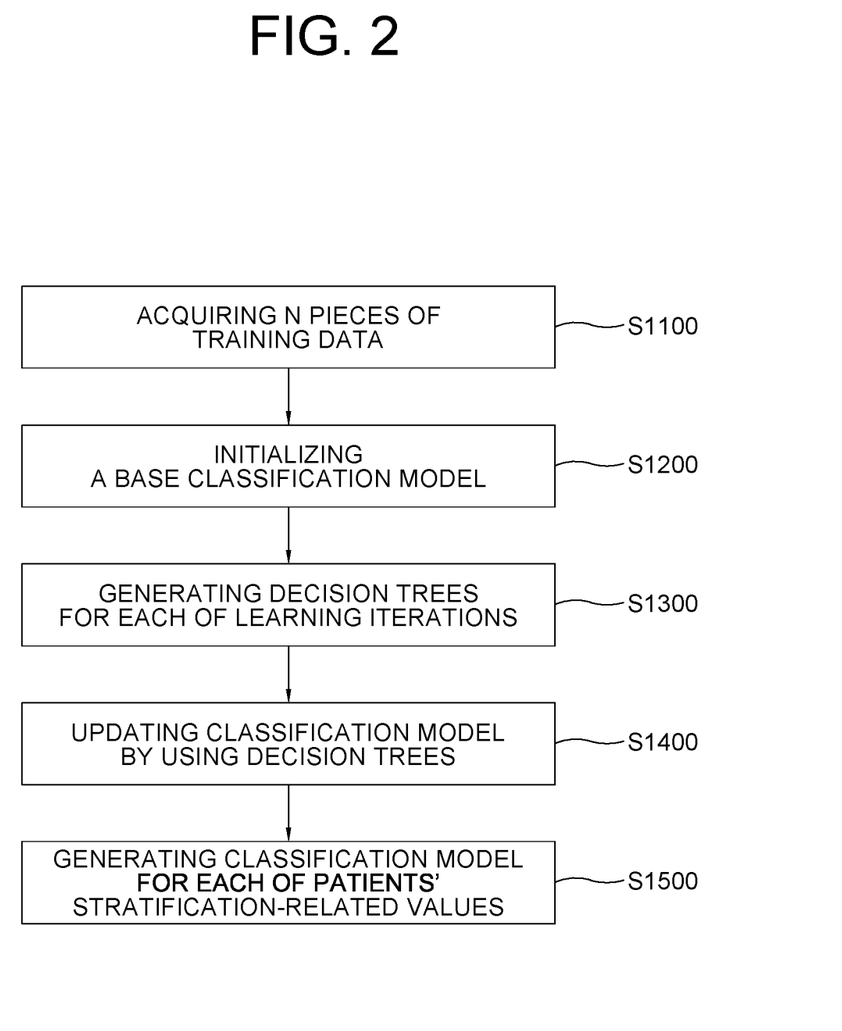
FIG. 2 is a drawing schematically illustrating a method for generating the diagnosis model capable of diagnosing multi-cancer according to the stratification-related values of patients by using the biomarker group-related value information in accordance with one example embodiment of the present disclosure.

First, as explained by referring to FIG. 2, on the condition that a diagnosis model 3100, including stratification-related value classification model 3200_1 to 3200_$q$ capable of classifying cancers by using the biomarker group-related value information for each of the stratification-related values, has been generated, the multi-cancer diagnosis device 2000 may acquire the certain stratification-related values and the certain biomarker group-related value information of the certain patient for diagnosing multi-cancer. The q may be an integer of 1 or more.

As an example, the multi-cancer diagnosis device 2000 may acquire the certain stratification-related values and the certain biomarker group-related value information of the certain patient from other devices or from user input(s) via the communication part.

Next, the multi-cancer diagnosis device 2000 may input the certain stratification-related values and the certain biomarker group-related value information of the certain patient into the diagnosis model 3100.

Then, the diagnosis model 3100 may instruct a certain stratification-related value classification model corresponding to the certain stratification-related values of the certain patient, among the first stratification-related value classification model 3200_1 to the q-th stratification-related value classification model 3200_$q$, to output certain cancer information which is a result of classifying cancers based on the certain biomarker group-related value information.

Therefore, in accordance with the present disclosure, via a classification model, which is the model for each of the stratification-related values of patients, capable of classifying cancer by having an effect only on a specific variable among the stratification-related variables according to a specific stratification-related values related to the specific variable, a process of diagnosing cancer may be performed in reliability.

The present disclosure has an effect of providing a diagnosis model capable of diagnosing cancers of patients for each of strata in which each corresponding variance is minimized by using biomarker group-related value information.

The present disclosure has another effect of recognizing types of cancers according to strata of patients accurately by using the biomarker group-related value information for diagnosing multi-cancer.

The present disclosure has still another effect of recognizing types of cancers according to the strata of patients accurately by statistical determination method using the biomarker group-related value information for diagnosing multi-cancer.

The present disclosure has still yet another effect of improving a reliability of determination of cancer according to the strata of patients by the statistical determination method using the biomarker group-related value information for diagnosing multi-cancer.

The embodiments of the present invention as explained above can be implemented in a form of executable program command through a variety of computer means recordable to computer readable media. The computer readable media may include solely or in combination, program commands, data files, and data structures. The program commands recorded to the media may be components specially designed for the present invention or may be usable to a skilled human in a field of computer software. Computer readable media include magnetic media such as hard disk, floppy disk, and magnetic tape, optical media such as CD-ROM and DVD, magneto-optical media such as floptical disk and hardware devices such as ROM, RAM, and flash memory specially designed to store and carry out program commands. Program commands include not only a machine language code made by a complier but also a high level code that can be used by an interpreter etc., which is executed by a computer. The aforementioned hardware device can work as more than a software module to perform the action of the present invention and they can do the same in the opposite case.

As seen above, the present invention has been explained by specific matters such as detailed components, limited embodiments, and drawings. They have been provided only to help more general understanding of the present invention. It, however, will be understood by those skilled in the art that various changes and modification may be made from the description without departing from the spirit and scope of the invention as defined in the following claims.

Accordingly, the thought of the present invention must not be confined to the explained embodiments, and the following patent claims as well as everything including variations equal or equivalent to the patent claims pertain to the category of the thought of the present invention.

What is claimed is:

1. A method for generating a diagnosis model capable of diagnosing multi-cancer according to stratification-related values of patients by using biomarker group-related value information comprising steps of:
   (a) a diagnosis model generating device, in response to acquiring n pieces of training data including (i) the stratification-related values corresponding to K stratification-related variables, (ii) the biomarker group-related value information and (iii) its corresponding Ground Truth cancer information for each of the patients, setting initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and
   (b) the diagnosis model generating device generating a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model,
   wherein, during a t-th iteration at the step of (b) wherein t is an integer of 1 or more and T or less, the diagnosis model generating device performs processes of:
   generating a t-th classification model capable of classifying cancers by (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree.

2. The method of claim 1, wherein the base classification model includes (i) a first classification model, which is a total classification model, capable of classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

3. The method of claim 2, wherein, at the step of (b), the diagnosis model generating device (i) makes a (t-1)-th total decision tree branch off from a (t-1)-th total classification model by using the total residuals corresponding to the n pieces of training data and a preset first normalization parameter such that a total correlation generated by referring to the total residuals and the first normalization parameter is maximized, (ii) makes (t-1)-th stratification-related variable decision trees branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) makes (t-1)-th stratification-related value decision trees branch off from a (t-1)-th stratification-related value classification model by using each of the total residuals corresponding to the n pieces of training data and a preset third normalization parameter such that each of stratification-related value correlations generated by referring to stratification-related value residuals corresponding to each of the stratification-related values and the third normalization parameter is maximized and (iv) generate a certain decision tree, that has the largest correlation among the (t-1)-th total decision tree, the (t-1)-th stratification-related variable decision trees and the (t-1)-th stratification-related value decision trees, as the t-th decision tree.

4. The method of claim 1, wherein, at the step of (b), the diagnosis model generating device updates the (t-1)-th classification model by applying at least one preset weight whose range is greater than zero and less than one to the t-th decision tree.

5. The method of claim 4, wherein the diagnosis model generating device applies the weight to a t-th decision tree classification model corresponding to the t-th decision tree and generates the t-th classification model by taking a sum of (i) the t-th decision tree classification model to which the weight has been applied and (ii) the (t-1)-th classification model.

6. The method of claim 1, wherein, at the step of (b), the diagnosis model generating device (i) generates losses by using the Ground Truth cancer information and the (t-1)-th cancer-predicting values and (ii) generates the total residuals by differentiating the losses.

7. A method for generating a diagnosis model capable of diagnosing multi-cancer according to stratification-related values of patients by using biomarker group-related value information comprising steps of:
   (a) on the condition that (1) a diagnosis model generating device, in response to acquiring n pieces of training data including (i) the stratification-related values corresponding to K stratification-related variables, (ii) the biomarker group-related value information and (iii) its corresponding Ground Truth cancer information for each of the patients, has set initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (2) the diagnosis model generating device has generated a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model, wherein, during a t-th iteration at the (2) wherein t is an integer of 1 or more and T or less, the diagnosis model generating device has performed processes of: generating a t-th classification model capable of classifying cancers by (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree to generate the t-th classification model, a multi-cancer diagnosis device acquiring certain stratification-related values and certain biomarker group-related value information of a certain patient; and (b) the multi-cancer diagnosis device (i) inputting the certain stratification-related values and the certain biomarker group-related value information into the diagnosis model and (ii) instructing the diagnosis model to output certain cancer information which is a result of classifying cancers based on the certain biomarker group-related value information via a certain classification model corresponding to the certain stratification-related values of the certain patient.

8. The method of claim 7, wherein the base classification model includes (i) a first classification model, which is a total classification model, classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

9. The method of claim 8, wherein, at the step of (a), by the diagnosis model generating device, (i) a (t-1)-th total decision tree has been made to branch off from a (t-1)-th total classification model by using the total residuals corresponding to the n pieces of training data and a preset first normalization parameter such that a total correlation generated by referring to the total residuals and the first normalization parameter is maximized, (ii) (t-1)-th stratification-related variable decision trees have been made to branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) (t-1)-th stratification-related value decision trees have been made to branch off from a (t-1)-th stratification-related value classification model by using each of the total residuals corresponding to the n pieces of training data and a preset third normalization parameter such that each of stratification-related value correlations generated by referring to stratification-related value residuals and the third normalization parameter is maximized and (iv) a certain decision tree has been generated such that the certain decision tree has the largest correlation among the (t-1)-th total decision tree, the (t-1)-th stratification-related variable decision trees and the (t-1)-th stratification-related value decision trees, as the t-th decision tree.

10. The method of claim 8, wherein, at the step of (a), by the diagnosis model generating device, the (t-1)-th classification model has been updated by applying at least one preset weight whose range is greater than zero and less than one to the t-th decision tree.

11. A diagnosis model generating device capable of diagnosing multi-cancer according to stratification-related values of patients by using biomarker group-related value information comprising:

one or more memories that stores instructions; and
at least one processor configured to execute the instructions to perform processes of (I) in response to acquiring n pieces of training data including (i) the stratification-related values corresponding to K stratification-related variables, (ii) the biomarker group-related value information and (iii) its corresponding Ground Truth cancer information for each of the patients, setting initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (II) generating a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model,
wherein, during a t-th iteration at the process of (II) wherein t is an integer of 1 or more and T or less, the processor performs processes of:
generating a t-th classification model capable of classifying cancers by (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree.

12. The diagnosis model generating device of claim 11, wherein the base classification model includes (i) a first classification model, which is a total classification model, capable of classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

13. The diagnosis model generating device of claim 12, wherein, at the process of (II), the processor (i) makes a (t-1)-th total decision tree branch off from a (t-1)-th total classification model by using the total residuals corresponding to the n pieces of training data and a preset first normalization parameter such that a total correlation generated by referring to the total residuals and the first normalization parameter is maximized, (ii) makes (t-1)-th stratification-related variable decision trees branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) makes (t-1)-th stratification-related value decision trees branch off from a (t-1)-th stratification-related value classification model by using each of the total residuals corresponding to the n pieces of training data and a preset third normalization parameter such that each of stratification-related value correlations generated by referring to stratification-related value residuals corresponding to each of the stratification-related values and the third normalization parameter is maximized and (iv) generate a certain decision tree, that has the largest correlation among the (t-1)-th total decision tree, the (t-1)-th stratification-related variable decision trees and the (t-1)-th stratification-related value decision trees, as the t-th decision tree.

14. The diagnosis model generating device of claim 11, wherein, at the process of (II), the processor updates the (t-1)-th classification model by applying at least one preset weight whose range is greater than zero and less than one to the t-th decision tree.

15. The diagnosis model generating device of claim 14, wherein the processor applies the weight to a t-th decision tree classification model corresponding to the t-th decision tree and generates the t-th classification model by taking a sum of (i) the t-th decision tree classification model to which the weight has been applied and (ii) the (t-1)-th classification model.

16. The diagnosis model generating device of claim 11, wherein, at the process of (II), the processor (i) generates losses by using the Ground Truth cancer information and the (t-1)-th cancer-predicting values and (ii) generates the total residuals by differentiating the losses.

17. A multi-cancer diagnosis device capable of diagnosing multi-cancer according to stratification-related values of patients by using biomarker group-related value information comprising:

one or more memories that stores instructions; and at least one processor configured to execute the instructions to perform processes of (I) on the condition that (1) a diagnosis model generating device, in response to acquiring n pieces of training data including (i) the stratification-related values corresponding to K stratification-related variables, (ii) the biomarker group-related value information and (iii) its corresponding Ground Truth cancer information for each of the patients, has set initial prediction values of a base classification model capable of classifying cancers for each of the stratification-related values by using the biomarker group-related value information, wherein the stratification-related values are generated by at least two stratification-related variables among the K stratification-related variables and wherein n and K are integers of 1 or more; and (2) the diagnosis model generating device has generated a first decision tree to a T-th decision tree by using its corresponding previous classification model, wherein the previous classification model has been updated by its corresponding previous iteration via a first iteration to a T-th iteration, and wherein the previous classification model represents the base classification model at the first iteration, to thereby generate the diagnosis model, wherein, during a t-th iteration at the (2) wherein t is an integer of 1 or more and T or less, the diagnosis model generating device has performed processes of: generating a t-th classification model capable of classifying cancers by (i) inputting the n pieces of training data into a (t-1)-th classification model which is the previous classification model at the t-th iteration and instructing the (t-1)-th classification model to output (t-1)-th cancer-predicting values which are results of classifying cancers for each of the n pieces of training data, (ii) generating each of total residuals corresponding to the n pieces of training data by referring to the Ground Truth cancer information for each of the patients and to the (t-1)-th cancer-predicting values, (iii) generating a t-th decision tree that maximizes a correlation with the total residuals and (iv) updating the (t-1)-th classification model by using the t-th decision tree to thereby generate the t-th classification model, acquiring certain stratification-related values and certain biomarker group-related value information of a certain patient; and (II) (i) inputting the certain stratification-related values and the certain biomarker group-related value information into the diagnosis model and (ii) instructing the diagnosis model to output certain cancer information which is a result of classifying cancers based on the certain biomarker group-related value information via a certain classification model corresponding to the certain stratification-related values of the certain patient.

18. The multi-cancer diagnosis device of claim 17, wherein the base classification model includes (i) a first classification model, which is a total classification model, classifying cancers by using all pieces of the biomarker group-related value information, (ii) a second classification model, which is a stratification-related variable classification model, capable of classifying cancers by using the biomarker group-related value information for each of the K stratification-related variables and (iii) a third classification model, which is a stratification-related value classification model, capable of classifying cancers by using the biomarker group-related value information for each of the stratification-related values.

19. The multi-cancer diagnosis device of claim 18, wherein, at the process of (I), by the diagnosis model generating device, (i) a (t-1)-th total decision tree has been made to branch off from a (t-1)-th total classification model by using the total residuals corresponding to the n pieces of training data and a preset first normalization parameter such that a total correlation generated by referring to the total residuals and the first normalization parameter is maximized, (ii) (t-1)-th stratification-related variable decision trees have been made to branch off from a (t-1)-th stratification-related variable classification model by using the total residuals and a preset second normalization parameter such that each of stratification-related variable correlations generated by referring to stratification-related variable residuals corresponding to each of the stratification-related variables and the second normalization parameter is maximized, (iii) (t-1)-th stratification-related value decision trees have been made to branch off from a (t-1)-th stratification-related value classification model by using each of the total residuals corresponding to the n pieces of training data and a preset third normalization parameter such that each of stratification-related value correlations generated by referring to stratification-related value residuals and the third normalization parameter is maximized and (iv) a certain decision tree has been generated such that the certain decision tree has the largest correlation among the (t-1)-th total decision tree, the (t-1)-th stratification-related variable decision trees and the (t-1)-th stratification-related value decision trees, as the t-th decision tree.

20. The multi-cancer diagnosis device of claim 18, wherein, at the process of (I), by the diagnosis model generating device, the (t-1)-th classification model has been updated by applying at least one preset weight whose range is greater than zero and less than one to the t-th decision tree.

* * * * *